United States Patent [19]

Somers et al.

[11] Patent Number: 5,328,484
[45] Date of Patent: Jul. 12, 1994

[54] NON-REUSABLE SYRINGE FOR MEDICAL PURPOSES

[76] Inventors: Brice Somers, 1, Chemin de al Sapiniére, 1253 Vandoeuvres; Eric Hauf, 55, Avenue de Rumine, 1005 Lausanne, both of Switzerland

[21] Appl. No.: 99,597

[22] Filed: Jul. 30, 1993

[30] Foreign Application Priority Data

Aug. 12, 1992 [CH] Switzerland .................... 2527/92
Jan. 28, 1993 [CH] Switzerland .................... 242/93

[51] Int. Cl.$^5$ .......................... A61M 5/32; A61M 5/00
[52] U.S. Cl. ................................ 604/195; 604/110; 604/196; 604/208
[58] Field of Search ............... 604/110, 195, 196, 263, 604/208, 238

[56] References Cited

U.S. PATENT DOCUMENTS

| | | |
|---|---|---|
| 1,592,462 | 7/1926 | MacGregor . |
| 2,457,859 | 1/1949 | Austin . |
| 2,474,496 | 6/1949 | Rayman . |
| 2,502,639 | 4/1950 | Blake . |
| 2,828,743 | 4/1958 | Ashkenaz et al. . |
| 3,320,954 | 5/1967 | Cowley . |
| 3,478,937 | 11/1969 | Solowey . |
| 4,026,287 | 5/1977 | Haller . |
| 4,391,272 | 7/1983 | Staempfli . |
| 4,592,744 | 6/1986 | Jagger et al. . |
| 4,655,751 | 4/1987 | Harbaugh . |
| 4,692,156 | 9/1987 | Haller . |
| 4,702,738 | 10/1987 | Spencer . |
| 4,720,285 | 1/1988 | Pickhard . |
| 4,740,205 | 4/1988 | Seltzer et al. . |
| 4,747,829 | 5/1988 | Jacob et al. . |
| 4,747,830 | 5/1988 | Gloyer et al. . |
| 4,770,655 | 9/1988 | Haber et al. . |
| 4,772,272 | 9/1988 | McFarland . |
| 4,781,683 | 11/1988 | Wozniak et al. ............ 604/110 |
| 4,790,822 | 12/1988 | Haining ..................... 604/195 X |
| 4,898,589 | 2/1990 | Dolgin et al. ............... 604/110 X |
| 4,950,241 | 8/1990 | Ranford ..................... 604/195 X |
| 4,950,251 | 8/1990 | Haining ..................... 604/195 |
| 4,952,206 | 8/1990 | Ibanez et al. ............... 604/110 |
| 5,019,043 | 5/1991 | Segui Pastor ............... 604/195 X |
| 5,152,750 | 10/1992 | Haining ..................... 604/195 |
| 5,171,300 | 12/1992 | Blake, III et al. .......... 604/195 X |
| 5,205,824 | 4/1993 | Mazur ........................ 604/195 X |
| 5,215,533 | 6/1993 | Robb .......................... 604/110 X |

FOREIGN PATENT DOCUMENTS

| | | |
|---|---|---|
| 8536/52 | 2/1954 | Australia . |
| 21012/53 | 5/1955 | Australia . |
| 25967/54 | 7/1955 | Australia . |
| 46410/59 | 3/1959 | Australia . |
| 13088/88 | 6/1990 | Australia . |
| 11436/88 | 8/1991 | Australia . |
| 0144483 | 6/1985 | European Pat. Off. . |
| 0326983 | 8/1989 | European Pat. Off. . |
| 0347742 | 12/1989 | European Pat. Off. . |
| 643616 | 4/1937 | Fed. Rep. of Germany . |

(List continued on next page.)

Primary Examiner—C. Fred Rosenbaum
Assistant Examiner—Frank Wilkens
Attorney, Agent, or Firm—Young & Thompson

[57] ABSTRACT

A syringe comprises a cylindrical body (1), a plunger (11, 15) movable linearly in the body (1), a needle carrier (28) also movable linearly in the body (1) and relatively to the plunger (11, 15) and a needle (24). The needle (24) before the use of the syringe is disposed inside a watertight cylinder (1) and is mounted on the needle carrier through a coupling of the snap on type which makes possible its separation from the needle carrier. The body (1) of the syringe is obturated at its distal end by a closing member (4) provided with an elastomeric plug (9) which can be perforated by the needle. The needle carrier (28) and the distal closing member (4) are provided with a coupling (31, 10) which cannot disengage once engaged. The rear end of the needle (24) and the plunger (11, 15) have a snap on coupling (20, 26) which cannot disengage once engaged. The minimal distance between the plunger (11, 15) and the needle carrier (28) is determined by a member (29), the resistance of which to compression is lesser in the moist or wet state than in the dry state.

12 Claims, 10 Drawing Sheets

FOREIGN PATENT DOCUMENTS

| | | |
|---|---|---|
| 85293156 | 5/1986 | Fed. Rep. of Germany . |
| 1005576 | 4/1952 | France . |
| 1039984 | 10/1953 | France . |
| WO88/06463 | 9/1988 | PCT Int'l Appl. . |
| WO89/04681 | 6/1989 | PCT Int'l Appl. . |
| WO89/10151 | 11/1989 | PCT Int'l Appl. . |
| WO90/05555 | 5/1990 | PCT Int'l Appl. . |
| WO90/06148 | 6/1990 | PCT Int'l Appl. . |
| WO91/00751 | 1/1991 | PCT Int'l Appl. . |
| WO91/08788 | 6/1991 | PCT Int'l Appl. . |
| 789027 | 1/1958 | United Kingdom . |
| 1511259 | 5/1978 | United Kingdom . |
| 2223411 | 4/1990 | United Kingdom . |

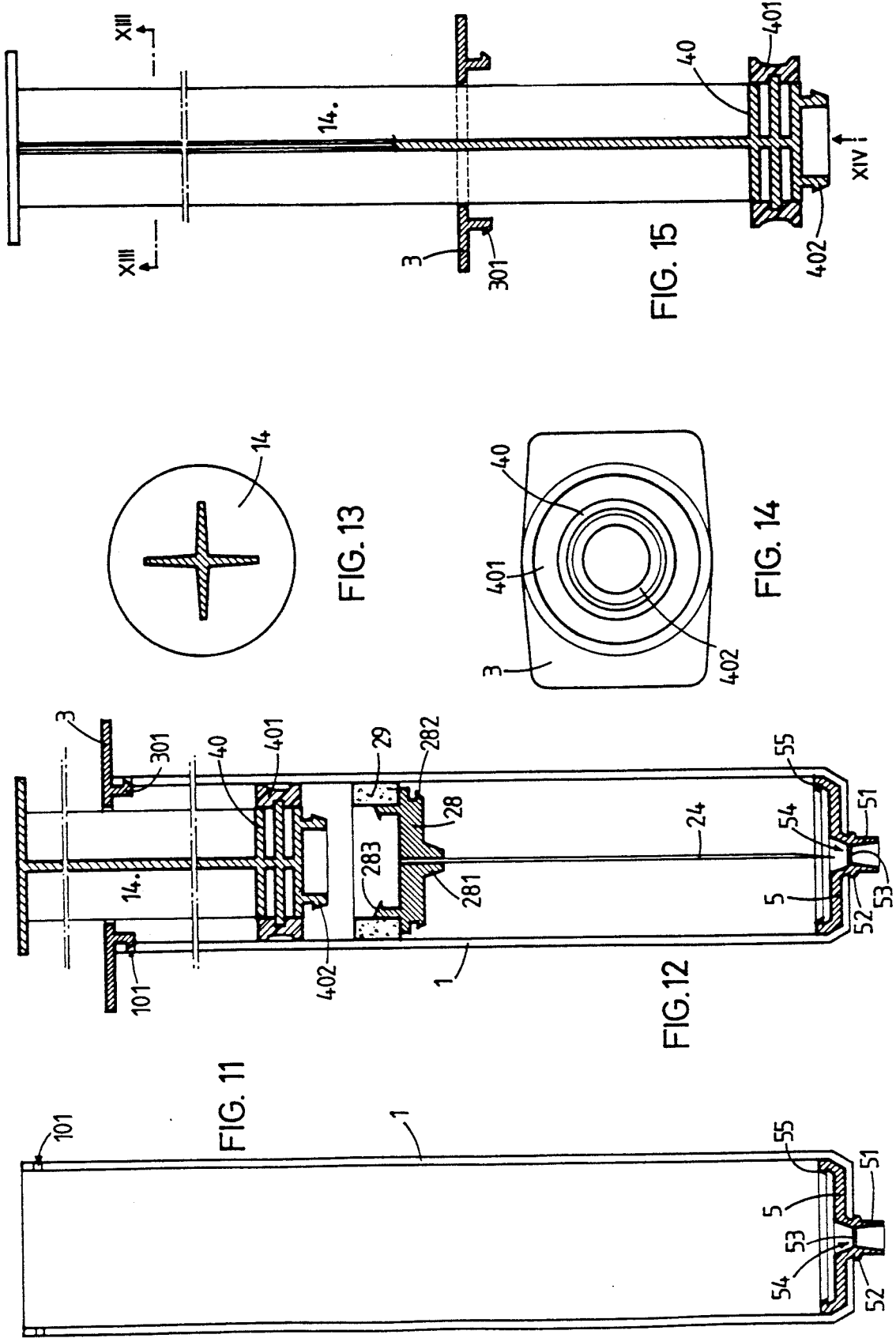

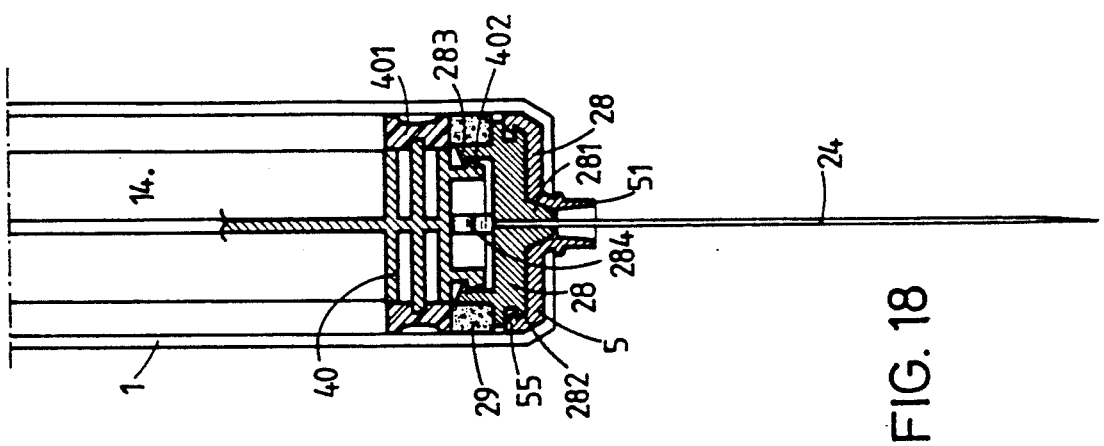
FIG. 18
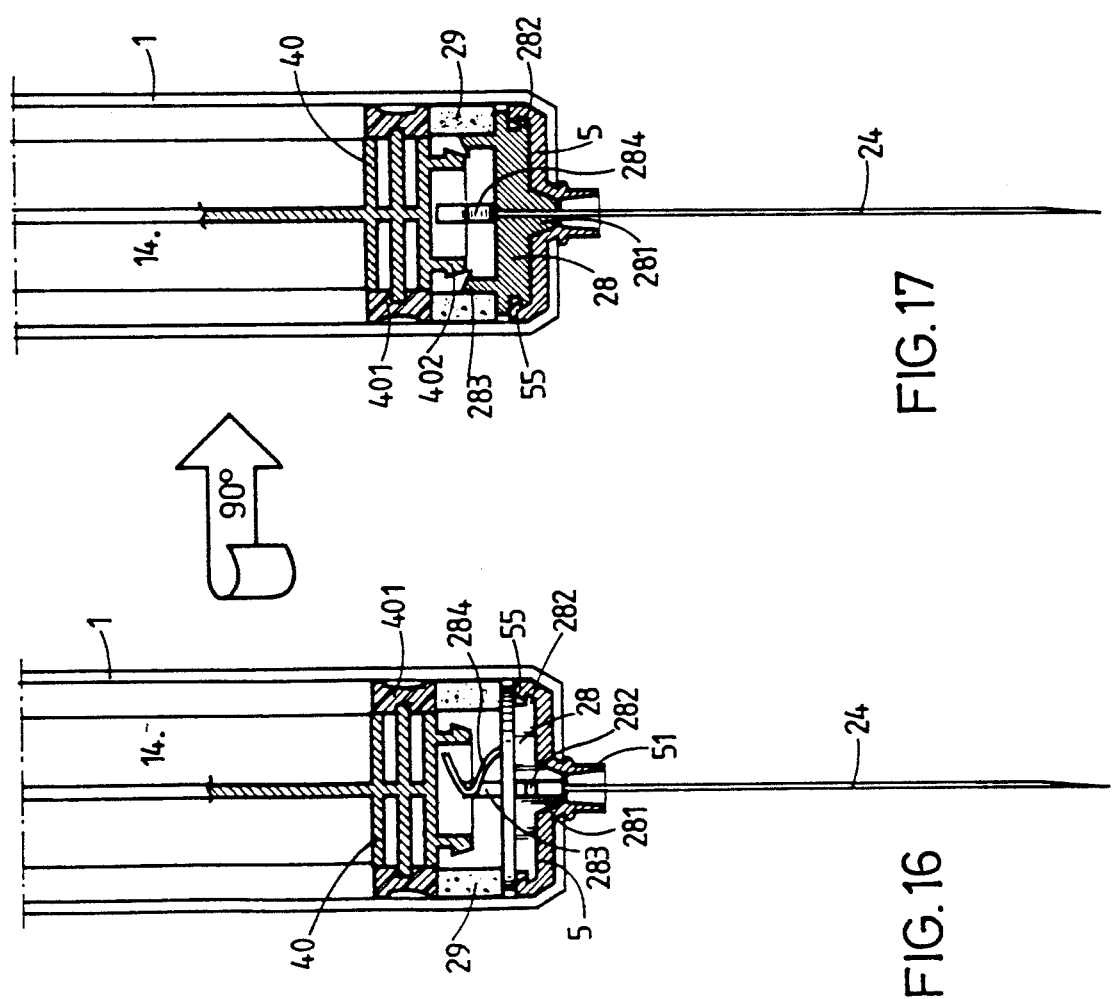
FIG. 17
FIG. 16

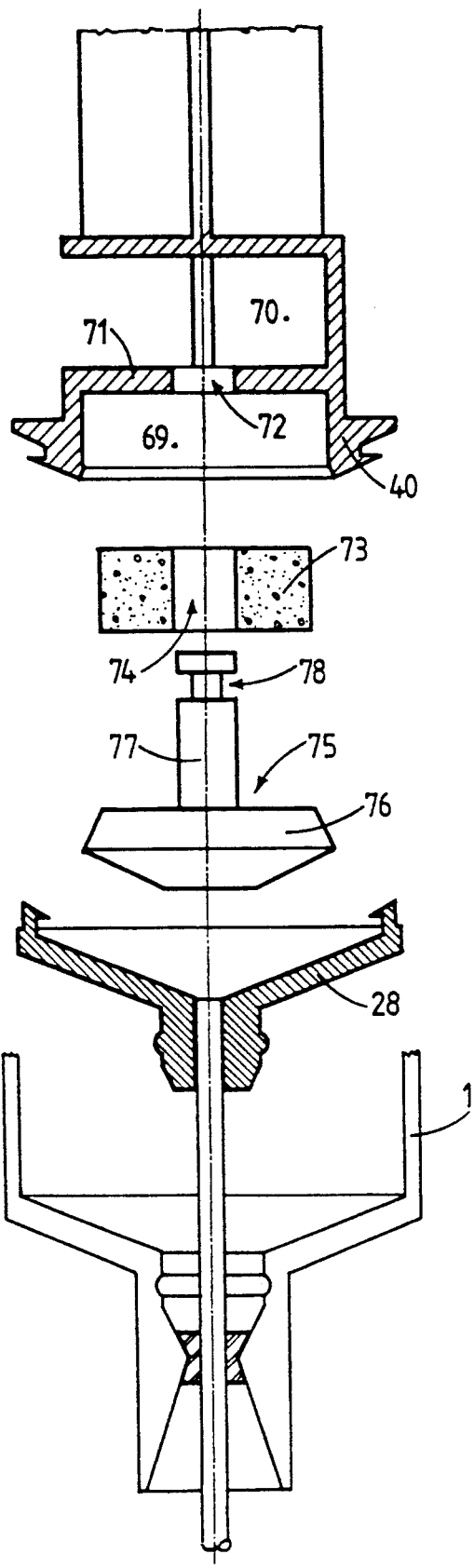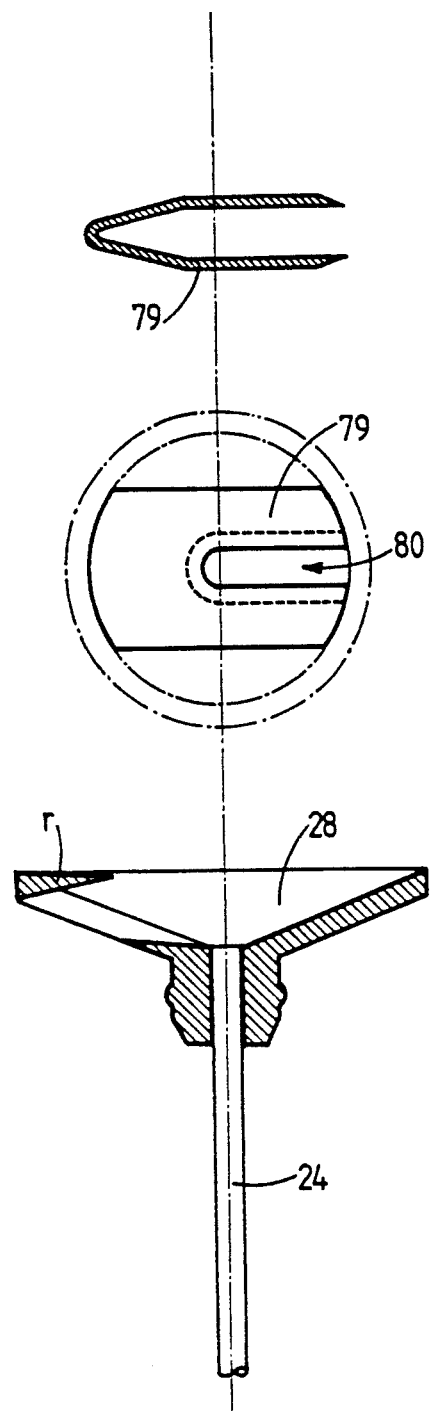
FIG. 25
FIG. 26

NON-REUSABLE SYRINGE FOR MEDICAL PURPOSES

The object of the present invention is a syringe for medical use, in particular a syringe which is totally safe for use not only by hospital and other medical staff, but also by patients, when they do the injections themselves. Accordingly, the syringe of the invention is designed to be totally safe to use, and in particular, to avoid all risks of contamination both of the medical staff and of the users or patients, to be easy to use and to be utilizable only once. Further, this new syringe is cheap to manufacture.

To this end, the invention consists of a syringe with a needle which is not apparent before use and which after use is retracted again inside the syringe cylinder, to avoid all hand manipulation of the needle and therefore all risks of contamination.

This syringe cannot be reused and can be disposed of after use without any particular precautions.

The cheap conventional syringes, though easy to use, are dangerous because of the risks of contamination when capping the needle (the user can stick himself) or in other later handling (for example during disposal).

Because of increasing risks of transmission via blood of diseases such as AIDS, viral hepatitis, syphilis, etc., new syringes have appeared which were designed for reducing the risks of contamination and for preventing their reuse. These syringes are more expensive and are more complicated to use than the conventional syringes, but the danger of contamination by a contaminated needle is not always excluded.

Amongst others, syringes of the brand name VACUTAINER are produced in the USA, VENOJET in Japan or VACUETTE in Holland. All these systems can only be used for sampling blood and require the introduction of a blood collector into the vein of the patient. Once this needle is in position, it is connected to an evacuated container or tube which then fills with blood.

In such systems, the needle itself needs to be held by the operator during its introduction into a vein, its connection to the tube or further during disposal, after use. All these manipulations are of a repetitive nature and further the disposal of the used syringes requires special precautions in terms of packaging, capping, etc.

Furthermore, such a system can only be used for sampling blood, and not for making injections.

Another drawback of this system resides in the fact that blood can be drawn only into tubes which had been previously evacuated. This implies that samples must be taken later with a conventional syringe, for example when transferring into a cultivation medium for carrying out hemocultures, which makes superfluous the use of the sophisticated system for preventing contamination.

When several tests need to be carried out, this requires that the whole operation of blood sampling with an evacuated tube be repeated. These repeated manipulations are unpleasant to the patient, who is forced to accept the continued presence of a collector inserted into a vein. Another drawback of these evacuated tube systems is that they must be made of glass and can therefore break.

Finally, the drawing of blood by the vacuum of a tube can, under certain special circumstances, cause the bursting of red blood cells or the obstruction of a vein due to a collapse of its walls, since it is not possible to adapt the level of suction or vacuum to the particular conditions of the patient.

Although the medical and the paramedical profession has become used to such systems based on evacuated tubes, they have nevertheless retained their preference for the conventional syringe, because of its simplicity. And in fact, with the present invention, all the simplicity of conventional syringes is retained, but without the risks of infection for the user.

Another system is known, which is the MONOVETTE manufactured in Germany, and which is similar to the VACUTAINER system, except that the evacuated collector tubes are replaced by cylinders provided with plungers very much similar to those of conventional syringes. Here, the risks of contamination are equally important.

A syringe is known from the document WO 90/06148, including a tubular body inside which moves linearly a plunger and a needle carrier and where the plunger and the needle carrier can be coupled and disconnected. Before use, the syringe is lodged inside the tubular body and is pushed out by a displacement of the needle carrier under the action of the plunger, against the bias of a spring, and is maintained ready to use in the protruding position by the needle carrier snapping on an internal shoulder of the body. Once in this position, the syringe can be used and reused as many times as wanted. By coupling the plunger with the needle carrier, it is possible to retract the latter at will inside the body, but this retraction of the needle is not automatic and must be deliberate. Further, the system is complicated and costly. This syringe cannot be provided sterilized, since it is open at the front.

Syringes are known from the documents EP 0 326 983 and EP 0 347 742 which also make it possible to retract at will the needle inside the body of the syringe after use. Here also, this operation is not automatic and needs to be deliberate, and hence the syringe can be reused. Further, before use, the needle of the syringe protrudes from the body and cannot therefore be sterilized without an additional protection.

The same drawbacks are found in the syringes described in the documents U.S. Pat. Nos. 4,507,117 and 4,675,005, i.e. the syringe cannot be sterilized without providing an additional protection since the needle protrudes from the body of the syringe before use and requires capping; on the other hand the retraction of the needle inside the body of the syringe must be deliberate, and hence the syringe can be used again. This syringe uses a metal spring mechanism and the needle cannot be separated from the needle carrier. Moreover, to remove the needle, a two way operation must be performed involving an axial and a rotatory movement of the plunger. Furthermore, the manufacturing cost is high.

The object of the present invention is a syringe which is aimed at obviating the drawbacks of known syringes and which satisfies in a manner which is simple, effective, sure and cheap the following requirements:

1. Before use, the syringe and its needle must be sterilized without the need to package them.
2. The syringe before use must have its needle enclosed hermetically inside the body.
3. The syringe must be usable both for drawing blood and for injecting products.
4. After having used only once the syringe and pulled the needle inside the body through a simple linear motion, it must be impossible to push out the needle again, to prevent any risks of later contamination or of reuse.

The disposable medical syringe of the invention which can only be used once obviates the above-mentioned drawbacks and which makes it possible to overcome the problems listed above, has the characteristics set forth in claim 1.

The appended drawings illustrate schematically and by way of example two embodiments of the syringe according to the invention.

FIGS. 11 to 20 show a third embodiment of the syringe.

FIGS. 21 to 26 show a fourth embodiment of the syringe.

Figure 3:
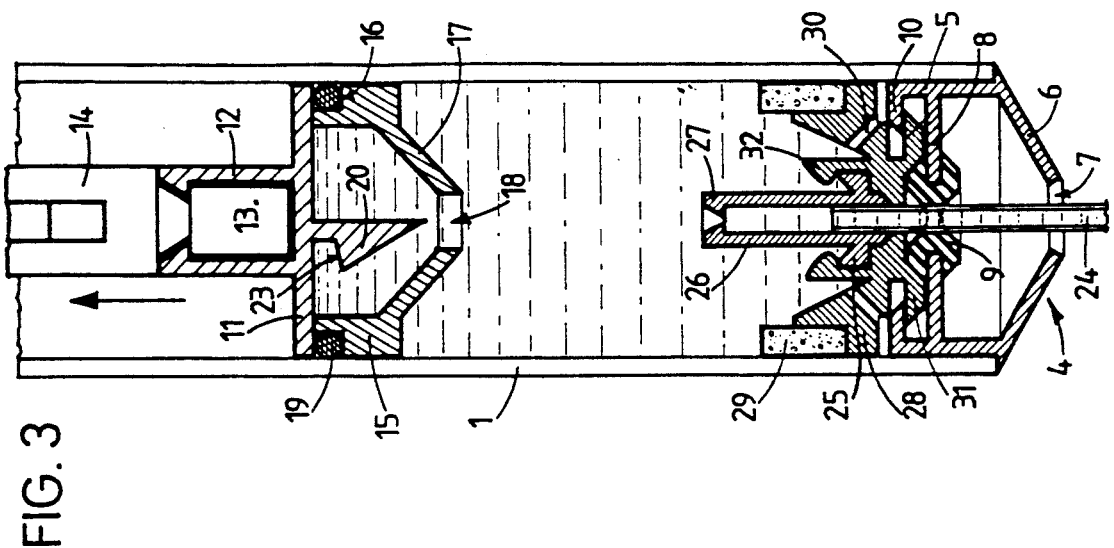
FIG. 3 shows the sampling or aspiration of a liquid or of blood with the syringe.

The object of the present invention is a medical syringe which can be used only once, either for sampling a liquid-generally blood-or for injecting a medicinal or some other solution. As will be seen from the following detailed description, this syringe offers numerous advantages by comparison with existing syringes, as well as by comparison with those not commercially available which have been described in the documents discussed in the introduction. These advantages are mainly:

1. The needle is an integral part of the syringe and cannot be separated therefrom, which avoids its direct manipulation, such as its mounting, capping, dismounting, storing, etc.
2. Before use, the needle is protected inside the cylinder which is closed hermetically. Hence, the syringe assembly can be sterilized after manufacture and assembling, for example by ionising radiations, without requiring any special packaging.
3. After use, the needle, which in some cases is separated from the needle carrier, is held by the plunger, which makes possible its automatic retraction inside the cylinder by the linear motion of the plunger. Thus, not only is the user protected against any risk of contamination or infection, but since the whole outer surface of the syringe is free of contamination, the syringe can easily be thrown away or disposed of without any special precautions, since any contaminated or soiled part would be hermetically enclosed within the cylinder. A single utilization is guaranteed, because the needle is biased automatically after its retraction inside the cylinder and cannot be intentionally pushed out again.
4. After use, the plunger is engaged permanently with the needle, which forbids any reuse of the syringe.
5. A cone at the end of the cylinder prevents any risk of contamination by a droplet of blood which may have remained on the outer surface of the elastomeric diaphragm.
6. After use, the rod of the plunger outside the syringe can be broken to reduce the bulk and to provide a further insurance that the syringe will not be reused.
7. The syringe is extremely simple to use and requires merely that the plunger be pushed linearly inside the cylinder and then pulled back, without any rotation, screwing, unscrewing or angular positioning of one part with respect to another one for actuating a coupling mechanism.
8. After use, the syringe can be disposed of without any special precaution, since its outer surface is not contaminated, and any contamination would remain sealed inside.
9. Finally, the construction of the syringe is simple and uses well-known and low-cost techniques. The syringe is entirely made of plastic by extrusion, molding or injection techniques, except for the needle of course, and this makes possible its high-speed mass production at low cost. The assembling is simple, can be automated and does not require skilled staff. The construction and assembling are simple without any springs or other complicated mechanisms, inexpensive and adaptable to industrial mass production.

Concerning the drawings, the first embodiment of the syringe illustrated in FIGS. 1 to 5 comprises a cylindrical tube 1 produced by extrusion, for example from transparent polycarbonate. This extruded tube is cut to the desired length according to the syringe capacity, to its convenience of use and to other usual factors.

This cylinder 1 of the syringe is closed at its proximal end by a cover, also made of plastic material comprising a central cylindrical portion 2 fitting snugly into the cylinder 1 and a flange 3 of a larger diameter. Once assembled, the cover 2, 3 is welded, fastened with an adhesive or by any other means to ensure the water-tightness of this proximal end of the cylinder 1 of the syringe.

The other end, the distal end of the cylinder 1 is obturated by a closing member 4 made by molding or injection from a thermoplastic resin, generally polystyrene. This closing member 4 includes a cylindrical part 5 of an external diameter corresponding to the internal diameter of the cylinder 1 and is fitted therein. The outer front portion 6 of this closing member 4 is truncated and provided with a central opening 7.

This opening 7 can be closed before the syringe is used by a plug or by a self-sealing film, which can subsequently be peeled off. One can also close this opening by a portion of the same synthetic material as that of the wall 6, but separated therefrom by a rupture line. This portion can include a tab, shaped for example as a ring, for tearing away this plug portion when the syringe is to be used and allowing the passage of the needle through the opening 7.

This closing member 4 is also sealed hermetically to the cylinder 1, by an adhesive, by welding or by any other appropriate means.

Since the material of the cylinder 1, the cover 2, 3 and the closing member 4 are compatible and can be produced by thermoforming, their assembling can be achieved by spin welding, which is very simple and fast.

The closing member 4 of the distal end of the cylinder 1 further includes a transverse wall 8 provided with a central opening. A ring or plug 9 made of an elastomer is molded on this transverse wall 8 so as to obturate this opening of the transverse wall 8 in a watertight manner. This plug 9 can include in its central part an area of lesser thickness designed to be punctured by the needle of the syringe, as will be seen later. This central front part of the plug 9 includes a recess designed for collecting any contamination from the external surface of the needle when the latter is retracted inside the cylinder, thus avoiding any dissemination of this contamination.

This distal closing member 4 further includes at the inside of the cylinder 1 of the syringe a retaining flange 10 having its inner edge chamfered, with the part of the opening of this flange 10 having the smallest diameter being located at the distal end of the syringe.

The syringe further includes a plunger made of a rear plate 11 provided with a female part 12 of a coupling. This female part 12 of a coupling extends through the central part 2 of the cover 2, 3 via an opening thereof and is accessible from the outside of the syringe. This female part 12 of the coupling is designed for cooperating with a male part 13 of a corresponding coupling located at the extremity of a rod 14 for actuating the plunger.

The plunger further includes a cylindrical skirt 15 in its upper part, having a diameter corresponding to the internal diameter of cylinder 1 and comprising a shoulder 16. The front part 17 of this skirt is truncated and is provided with a central opening 18. The plate 11 having the coupling part 12 and the skirt 15, 16, 17 are fixed together rigidly by welding, by an adhesive, etc. These parts are made of a thermoplastic material such as polyacetal and are formed by molding or by injection. An O-ring 19 is placed in a groove formed between the shoulder 16 of the skirt and the plate 11, to ensure perfect watertightness between this plunger 11-19 and the cylinder 1.

Figure 6:
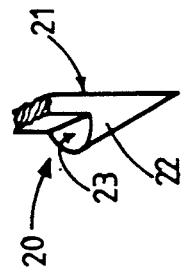
FIG. 6 is a detail of the hook of the plunger.
Figure 7:
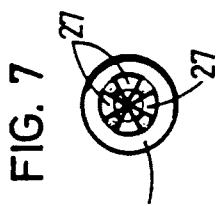
FIG. 7 is a plan view of the rear part of the needle.
Figure 8:
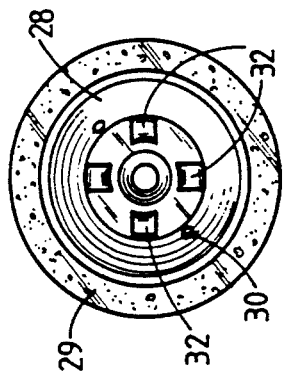
FIG. 8 is a plan view of the needle carrier.
Figure 5:
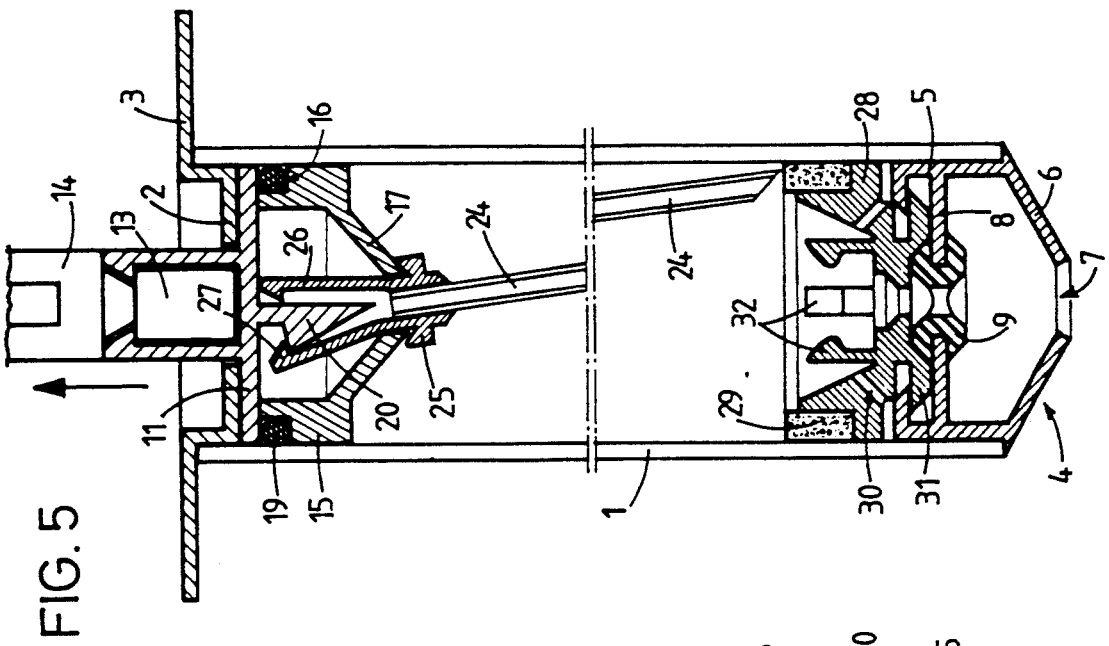
FIG. 5 shows the syringe after use, with the needle enclosed again inside the body.
Figure 4:
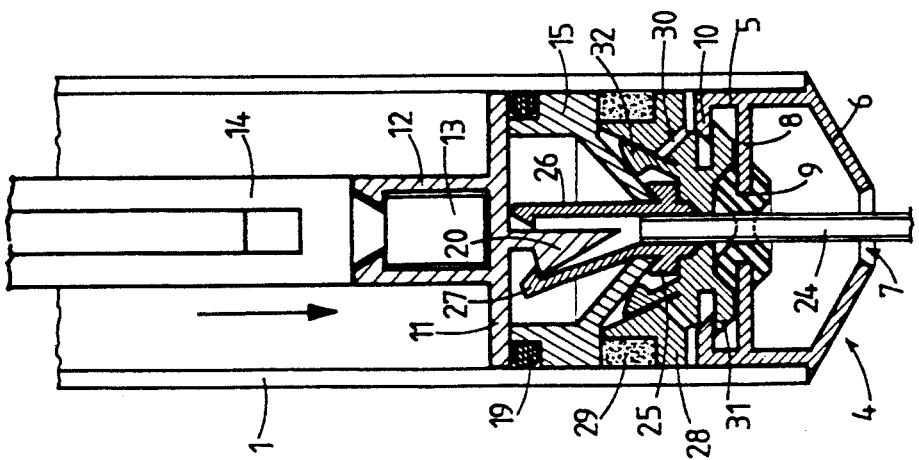
FIG. 4 shows the state of the syringe after expulsion of the blood sampled, into a test tube or into some other container, or after the injection of the liquid into the body.

This plunger further comprises a hook 20 integral with the plate 11 and extending inside the skirt 15, 17. This hook has in the embodiment illustrated (FIG. 6) a flat face 21 in the axis of cylinder 1 and a retaining member formed as a half-cone 22, the diameter of which increases in the direction of the plate 11, which half-cone ends by a flat face 23 sloping slightly with respect to plate 11.

This syringe further includes of course a hollow needle 24 made of steel with a chamfered tip and which is provided at its proximal end with a molded component made of a thermoplastic material, for example of polyacetal, and which comprises on the one hand a disk 25 the upper face of which is recessed in such a manner that its outer edge forms a retaining member as will be seen further and, on the other hand, tabs 26 (four in the embodiment illustrated) provided with hooks 27 at their end. These tabs 26 are flexible and run in their normal position parallel to the axis of the needle along a circumference, the diameter of which corresponds to that of the central opening 18 of the plunger, so that they can penetrate inside the internal space of the skirt 15, 17. The length of these tabs 26 is sufficient for at least one of these hooks 27 to grip the flat face 23 of the hook 20 of the plunger when fully introduced inside the skirt 15, 17, so as to interlock the needle 24 permanently with this plunger 11, 22.

The needle 24 and its molded component 25, 26, 27 are normally mounted on a needle carrier sliding freely inside the cylinder 1. This needle carrier comprises a rigid body 28 of a diameter corresponding to the inner diameter of the cylinder 1 and is provided with an annular recess facing the proximal end of the syringe, for receiving a ring 29. The body 28 is made of a synthetic material such as polyacetal and is formed by molding or injection. The body 28 further includes at least one passage or vent 30 for communication of the two parts of the cavity of cylinder 1 on both sides of this needle carrier, so that the latter may slide freely in the cylinder 1.

This movable needle carrier further has first snap on means 31 on its distal face which consist of tabs or pawls with a chamfered face and which, when they are applied against the flange 10 of the distal closing member deform elastically and snap on this flange 10 to ensure a permanent and irreversible interlocking of the needle carrier and of the distal closing member.

The needle carrier further has second snap on means 32 extending from the body 28 in the direction of the proximal end of the syringe and cooperating with the edge of the disk 25 of the molded component of the needle. This snap on means 32 consists of elastically deformable tabs which are provided at their ends with extensions cooperating with the edge of the disk 25. The coupling thus obtained is reversible and, as will be seen further, the needle and its molded component can be separated from the needle carrier during the operation of the syringe.

Actually, the molded component 25 of the needle must be coupled with the needle carrier 32 with a strength sufficient to prevent disengagement of these parts during the introduction of the needle inside a vein or a muscle of the patient. On the other hand, this coupling must be sufficiently weak to allow the separation of the needle from the needle carrier, when the needle is coupled with the plunger and the latter is pulled back.

The ring 29 placed inside the annular recess of the body 28 of the needle carrier is made of a natural or synthetic porous material which is rigid when dry but which can soften upon contact with a liquid it adsorbs.

Before use, the ring 29 is dry and hard and offers therefore an appreciable resistance to compression. The height of this ring 29 is such that when the plunger is moved in the direction of the needle carrier, the upper face of this ring 29 abuts against the lower face of the cylindrical part 15 of the skirt because of the resistance of the ring 29 of the plunger, and the hooks 27 of the tabs 26 of the molded component of the needle 24 cannot rise sufficiently along the hook 20 of the plunger to become engaged with the face 23 thereof. Thus, when the ring 29 is dry and hard or rigid, it is not possible to snap the component 25, 26 of the needle 24 on the hook 20 of the plunger. As will be seen further, this snapping on operation is possible when the ring 29 is softened by a liquid, since the alveolated or expanded structure from which it is made loses its rigidity, its hardness and its resistance to compression.

According to the detailed description made of the syringe, the latter comprises a cylinder 1 closed at both ends before its use and three components contained inside the cylinder, namely the plunger 15, the needle 24-25 and the needle carrier 31-32, all three being movable with respect to the cylinder and relatively to each other. Further, the needle carrier 31 can be coupled in an irreversible and permanent manner with the distal end of the cylinder 10; the needle can be coupled in an irreversible and permanent manner with the plunger and the needle is coupled in a disengageable manner with the needle carrier.

This syringe includes a member located between the plunger and the needle carrier, of which the hardness and therefore the resistance to compression decreases when it is exposed to a liquid, this member making possible the coupling of the needle with the plunger only when its resistance has decreased following exposure to a liquid.

The operations of the syringe described are as follows:

1. The user takes a new sterile syringe, such as the one illustrated in FIG. 1 and if the rod is not integral with the plunger, he engages the rod 14 with the plunger 11-23 of the syringe by means of the snap on coupling 12, 13 and releases the opening 7.

2. By pressing on the rod 14 and by holding the body of the syringe by the flange 3, the user moves the plunger 11-23 in the direction of the distal end of the syringe. In this process, the cylindrical part 15 of the skirt of the cylinder presses against the ring 29, which is rigid and resistant since it is dry, of the needle carrier 28-32 and hence drives the needle carrier, as well as the needle 24-26 engaged therewith. In this operation, the chamfered and sharp end of the needle 24 pierces the elastomeric plug 9 and the needle protrudes from the cylinder 1.

Figure 2:
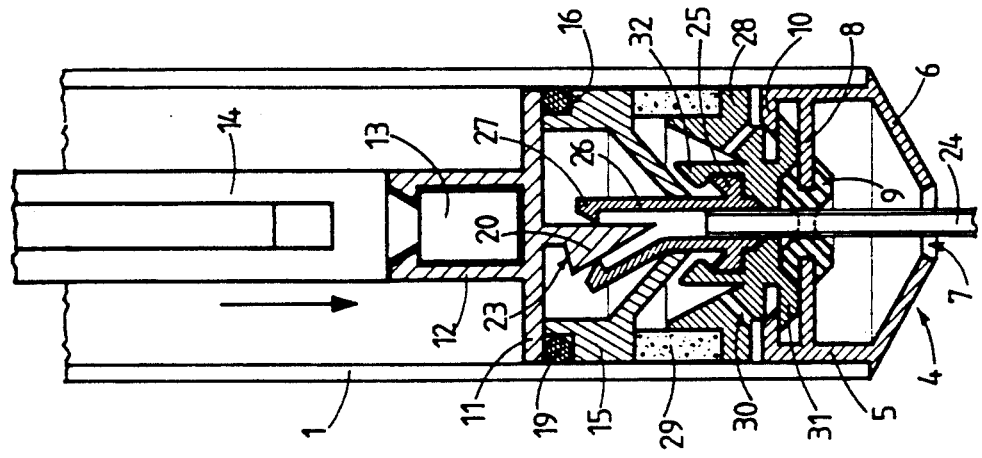
FIG. 2 shows the syringe ready for use.
Figure 1:
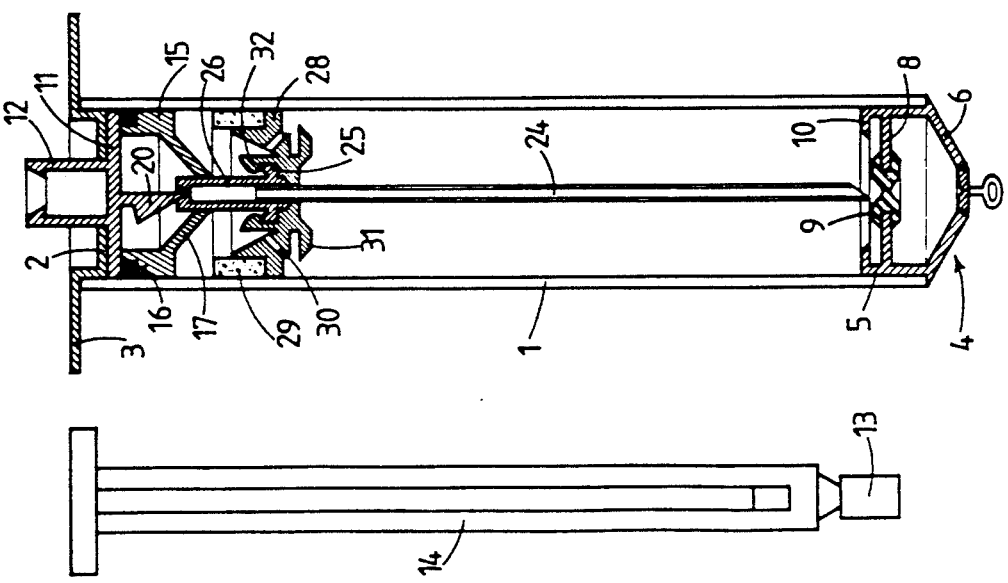
FIG. 1 shows a syringe according to the invention before use, with its rod disconnected.

The user continues to move the plunger towards the distal end of the syringe until the syringe carrier becomes rigidly and permanently connected to the distal closing member 4 by the hooking of the pawls 31 moving under the flange 10 (see FIG. 2). During this movement of the plunger, of the needle carrier and of the needle, the air contained in the cylinder flows through the needle carrier via the passages or vents 30 and exits from the syringe via the central bore of the needle 24. As can be seen in FIG. 2, the molded component of the needle 24 could not engage with the plunger, because the distance between the plunger and the needle carrier is maintained sufficiently far by the ring 29. It should be noted that in this position, perfect watertightness is ensured between the front face of the needle carrier and the plug 9, which is made of an elastomer and can therefore undergo an elastic compression.

3. The user places the needle 24 either inside a container, flask, test tube, etc, from which a liquid is to be drawn, or the needle is introduced inside the vein of a patient. Then, by moving the plunger 12-13 in the direction of the proximal end of the syringe, he draws the liquid or blood, through the needle and inside the cylinder 1 between the needle carrier permanently fixed to the cylinder and the plunger (FIG. 3). At the end of the distance the plunger can travel, or when the desired amount of liquid or blood is drawn, the user moves the needle from the container or from the patient's vein.

4. In the case where blood was taken from a patient, the user places the needle inside a test tube, and when the syringe is filled with a liquid, the user introduces the needle into the vein, muscle, etc. of the patient. The user then moves the plunger in the direction of the distal end of the syringe, thus emptying the content thereof into one or several test tubes, or into the vein, muscle, etc. of the patient.

By the time the ring 29 of the needle carrier has reached the end of the distance it can travel (FIG. 4), it has become soft through the contact with the liquid or the blood contained in the syringe, and the plunger moves further until the conical part 17 of the skirt abuts against the disk 25 of the molded component of the needle and at least one of the hooks 27 of the tabs 26 of the molded component engages with the face 23 of the hook 20 of the plunger. In this process, the second snap on means 32 of the needle carrier are spread apart by the truncated portion 17 of the skirt of the plunger and when the user moves the plunger again in the direction of the proximal end of the syringe, the latter pulls the needle which separates from the needle carrier. When the plunger reaches the end of the distance it can travel (FIG. 5), the needle 24 is entirely retracted inside the cylinder 1 with its end located above the needle carrier which is now permanently locked with the distal closing member. The plug 9 which is made of an elastomer closes, so that the cylinder of the syringe is hermetically closed again.

Further, owing to the conical shape of the hook 20 of the plunger and of its offset with respect to the axis of the cylinder, the needle deviates under the elastic pressure of the tabs 26 to form an angle of for example 5° to 7° with respect to the axis of the cylinder. This excludes any possibility that the needle after use may emerge again from the cylinder of the syringe. To further increase or guarantee this deviation of the needle, it is possible to construct the front face of the skirt 17 of the plunger at an angle so that this front face be for example parallel to the gripping surface 23 of the hook 20. In this manner, the pressure of the skirt 17 against the disk 25 of the component molded on the needle will also force the needle in its retracted position to deviate sideways.

It can hence be seen that the use of the syringe for the operator is very simple, only linear movements are needed between the rod 14 and the cylinder 1. All the coupling operations required take place automatically and without the user having to worry about the relative angular position of the parts to be coupled. At the end of the distance the plunger can travel when expelling the liquid contained in the syringe, the needle and the plunger are engaged automatically and irreversibly, so that a second utilization of the syringe is impossible; in fact, to refill the syringe, one must pull the plunger back, whereby the needle is automatically pulled back into the cylinder and blocked therein.

All the components which had been in contact with the blood or another liquid and which could hence be contaminated are enclosed hermetically at the end of the process and the syringe can be disposed of without any other precautions.

It should further be noted that during and after use, both hands of the user are always on the proximal side of the syringe, i.e. the one which is not dangerous: one hand holds the cylinder and the other pulls the plunger which draws the needle inside the cylinder. The other systems require that one of the user's hands be at the distal side of the syringe or of the collector in order to cover with a cap the needle which is contaminated or even to unscrew it from the body of the syringe, which is the most dangerous moment because of the risks of the user suffering a needle stick injury and contaminating himself. The present syringe is therefore much safer to use than existing traditional systems.

Figure 9:
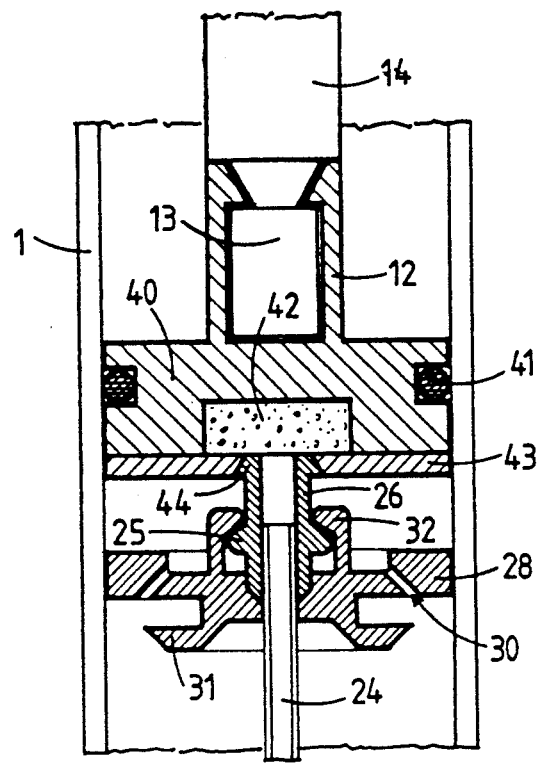
FIG. 9 is a view similar to that of FIG. 1 of a second embodiment of the syringe.
Figure 10:
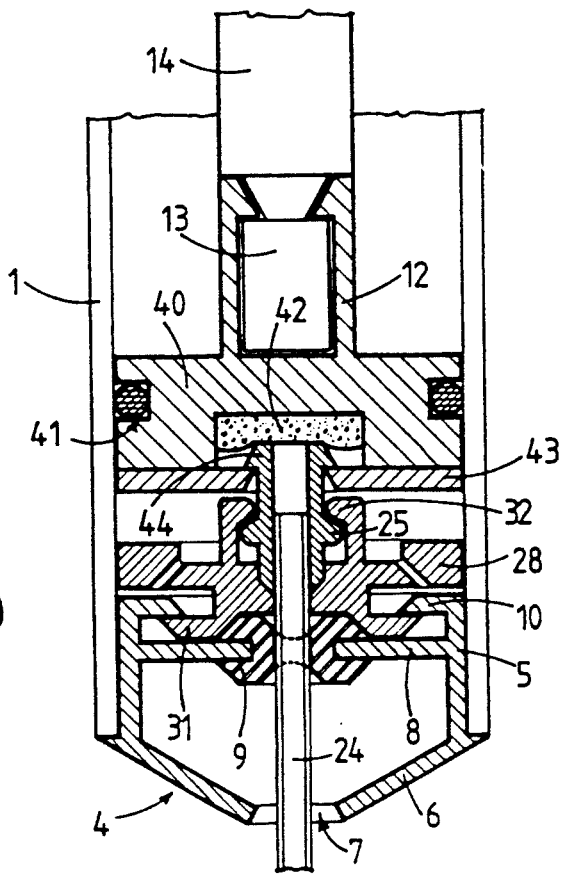
FIG. 10 is a view similar to that of FIG. 4 of the second embodiment of the syringe.

In the second embodiment of the syringe illustrated in FIGS. 9 and 10, substantially all the components already described are to be found, only the coupling between the plunger and the needle, and further the position of the member of which the hardness or resistance can be modified being different.

In this embodiment, the plunger sliding in the cylinder 1 has a body 40 provided with a groove 41 for receiving an O-ring. The upper face of this plunger is provided with the coupling part 12 of the rod 14, whereas the distal face of the body 40 comprises a housing containing a block 42 made of an expanded synthetic material or of a cellular natural material, which can soften upon contact with a liquid. A plate 43 fastened rigidly by an adhesive, welding, etc, against the distal face of the plunger holds the porous member 42 in position and includes a passage which has chamfered edges and which becomes narrow in the direction of the member 42.

The tabs 26 of the component molded on the needle 24 have hooks 44 designed for penetrating inside the housing of the body 40 when the member 42 is softened by a liquid and for engaging permanently behind the plate 43 of the plunger (FIG. 10).

The operations of this second embodiment of the syringe are in all points identical to those of the first embodiment described and offer accordingly the same advantages. In this embodiment, in order to provoke during the retraction of the needle 24 inside the cylinder its displacement sideways for preventing it from being pushed out of the cylinder, it is possible to confer different lengths to the tabs 26 or to confer a slant to the upper face of the plate 43.

In any case, even if the needle is not oriented at an angle after use with respect to the axis of the cylinder, the syringe cannot be used because the needle is locked permanently with the plunger and moves with it. Further, its upper end being closed by the plunger, it is impossible to fill and empty the cylinder by a back and forth motion of the plunger.

In the third embodiment illustrated in FIGS. 11 to 20, the needle 24 is carried by the needle carrier 28 and fastened fixedly thereto. It is this needle carrier 28 which carries snap on coupling means for permanent engagement with the distal closing member 5 as in the first embodiment. This needle carrier 28 also has on its other face directed towards the plunger 40, snap on coupling means which engage permanently with the plunger. In this embodiment, the member with a variable resistance 29 is a ring carried by or fastened to the upper face of the needle carrier which is directed towards the plunger.

This third embodiment is particularly advantageous in that it is made of few components, which can all be obtained by injection and assembled automatically.

FIG. 11 shows the cylinder 1 of the syringe obtained by injection in which is housed the distal closing member 5 made of an elastomer which is relatively rigid. This distal closing member includes a central tubular extension 51 protruding from the cylinder 1 via a frontal hole thereof. This distal closing member 5 is maintained in its operative position by a bead 52 which was forced through the central hole of the cylinder to prevent any later separation of these two parts. The central tubular extension 51 is closed before the syringe is used by a wall or a membrane 53 which is pierced by the needle 24 when the latter is pushed out of the cylinder 1.

In FIG. 12, it can be seen that in this third embodiment, the needle 24 is rigidly fastened on a needle carrier 28, formed by molding or injection. The distal lower face of this needle carrier 28 has a shape which matches that of the internal proximal face of the closing member 5. In particular, a conical extension 281 and a snap on means 282 match the opening 54 and the retaining means 55 of the distal closing member 5.

These snap on means 55, 282 make possible a temporary engagement which is sufficiently strong to resist the pushing of the needle 24 inside a muscle or a vein of a patient or for puncturing the plug of a container, but which nevertheless can be disengaged so that the plunger 40 may pull the needle 24 back inside the cylinder after use.

The rear or proximal face of the needle carrier 28 is provided with snap on means 283 arranged concentrically with a space for receiving the member with a variable resistance 29 which here has the shape of a ring or of an annulus.

The plunger 40 and its rod 14 are made as a single part by injection and it has on its periphery a seal 401 which ensures the watertightness with cylinder 1. On its free distal face, this plunger has snap on means 402 designed for cooperating with the snap on means 283 of the needle carrier 28 and for providing therewith a connection which once engaged is permanent and irreversible.

The rear end of the body or cylinder 1 is closed by a plate 3 which, before use is made of the syringe, is connected by tabs which can be broken, to the rod 14 of the plunger. These tabs guarantee when they are intact that the syringe has not been used. The proximal plate or closure 3 of the syringe is fastened to the cylinder by the engagement of the hooks 301 inside the holes 101 arranged in the cylinder 1.

FIGS. 13, 14 are a cross-sectional view of the rod 14 of the plunger and a view of the distal end of the plunger, respectively.

FIG. 15 is a view of the plunger 40, of its rod 14 and of the proximal closing plate 3, before assembling with the cylinder 1.

Before use, the syringe is as shown in FIG. 12. To use the syringe, the operator pushes the plunger 40 by its rod 14 inside the cylinder 1 and in the process, he breaks the portions connecting the rod 14 to the plate 3.

The distal face of the plunger 40 presses against the ring 29 and pushes the needle carrier 28 and the needle 24 in its movement. The needle 24 pierces the elastomeric membrane 53 and the needle carrier becomes engaged with the front closing member 5 (FIGS. 16 and 17). The ring 29 is dry and therefore rigid and cannot be compressed, and this avoids all risks of engagement of the plunger 40 with the needle carrier 28. From this moment, the syringe is ready for use, the user can either fill the cylinder with the blood of a patient, or with a liquid from a flask, by moving the plunger in the cylinder in a proximal direction.

As in the embodiments described previously, as soon as the ring 29 is in contact with a liquid, it looses its rigidity and when the plunger 40 is moved again in the direction of the needle carrier, the two become permanently interlocked (FIG. 18) when the plunger reaches the end of the distance it can travel. From then on, the syringe cannot be used any more since the plunger and the needle can only move simultaneously together.

Figures 19, 20:
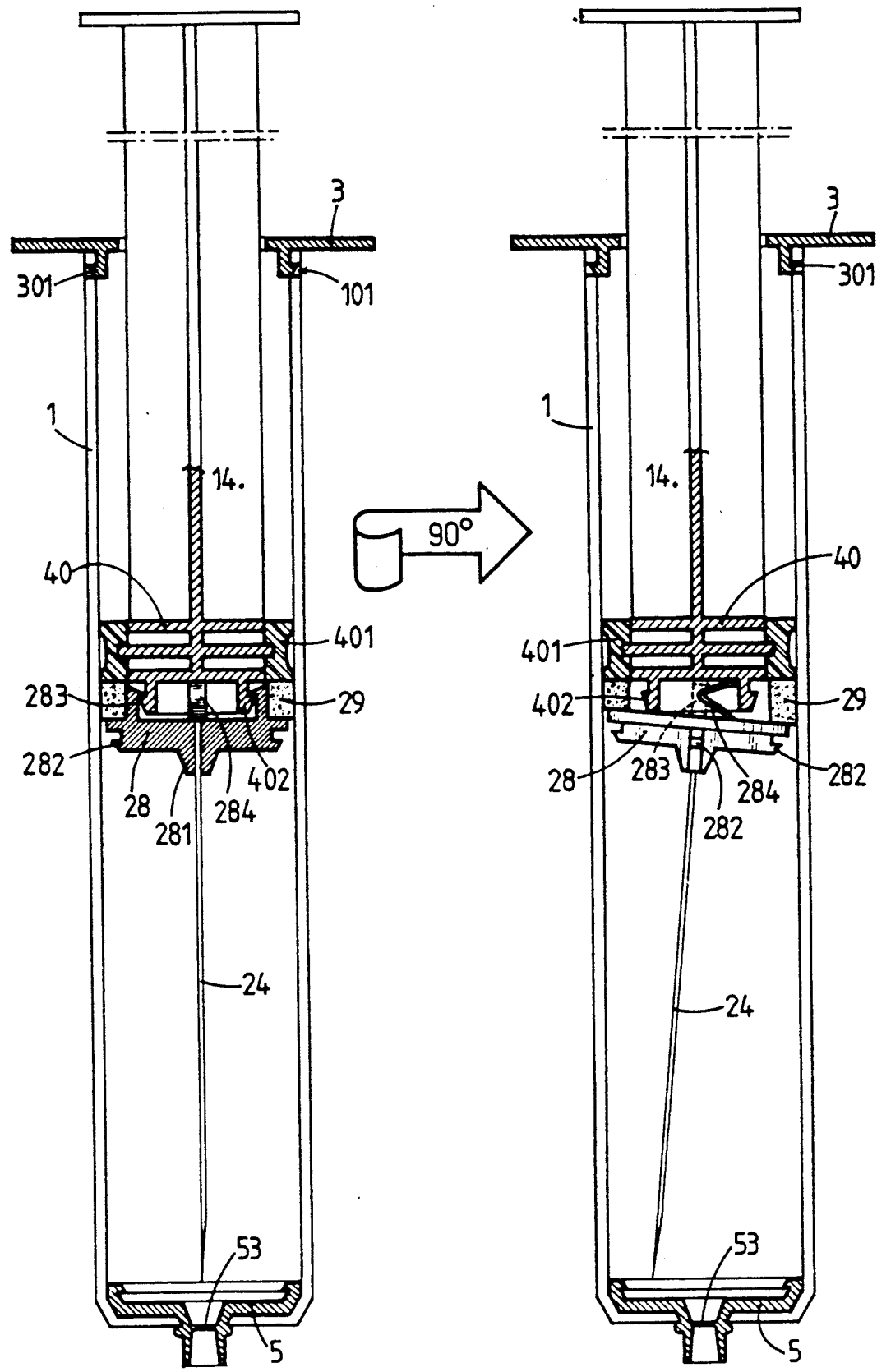
Figure 21:
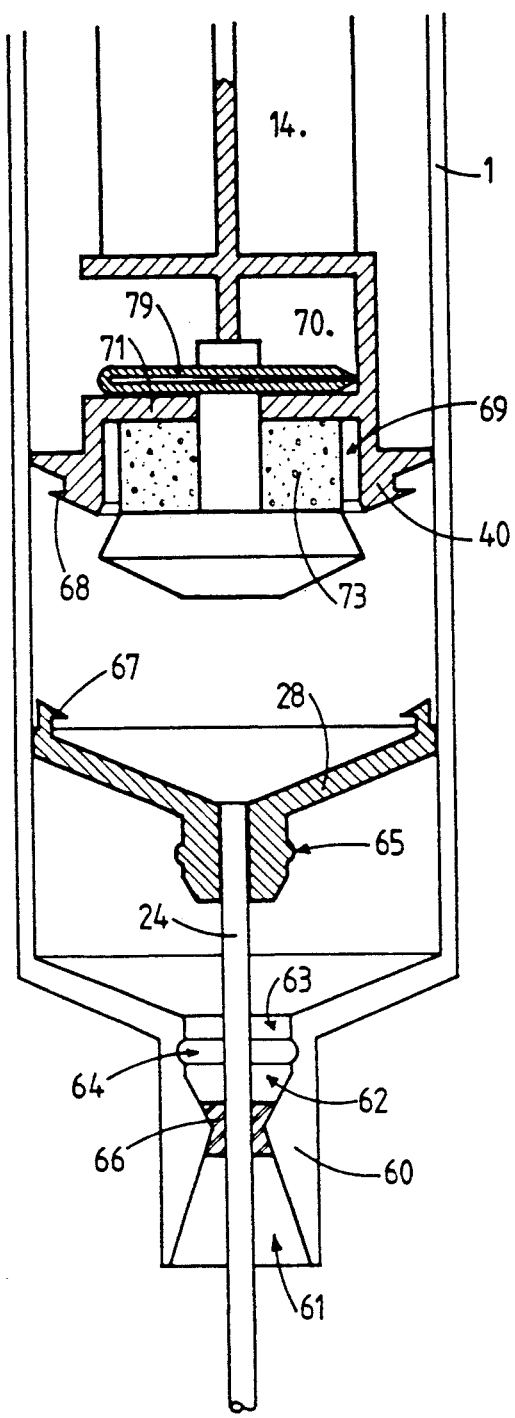

Thus, by pulling the plunger by its rod, the needle carrier 28 and the needle 24 are moved inside the cylinder, the needle carried being disengaged from the proximal closing member 5, which causes the needle to retract inside the cylinder (FIGS. 19, 20). As soon as the needle 24 is wholly inside the cylinder, the elastomeric membrane 53 closes again the front end of the cylinder and the needle is deviated inside the cylinder under the effect of the resilient blade 284 included in the needle carrier 28. From then on, it is impossible to push the needle 24 out of the cylinder 1 again. This deviation of the needle can be brought about by other means, for example by the own elasticity of the ring 29 or by the shape of the proximal surface of the needle carrier.

The fourth embodiment of the syringe, FIGS. 21 to 26 according to the invention is still based on the same principle as described previously and its operations are in all points similar. However, this embodiment, which also is made of even fewer parts, enables a further decrease of the amount of plastic material used and a simplification of the shape of the parts.

In this embodiment, the syringe also has a hollow cylinder 1 and a plunger 14, the upper parts of which can be made as in the third embodiment.

The lower end of the cylinder has a cylindrical extension of a smaller diameter 60 having a passage of a particular shape. Actually, this passage connecting the inside of the cylinder 1 and the outside of the syringe has at its distal end a truncated portion 61 which becomes more narrow in the direction of the cylinder 1, followed by a reversed truncated portion 62 which becomes larger in the direction of the cylinder 1. The intersection of these two portions 61 and 62 of the passage defines a constriction in said passage. This passage has a further third portion 63 connecting the truncated portion 62 to the inside of the cylinder 1. This portion 63 has a generally cylindrical shape and a groove 64 of an increased diameter, and provides one part of the disengageable snap on coupling between the needle carrier 28 and the cylinder 1. The other part of this coupling carried by the needle carrier 28 is formed as a circular bead 65 formed on the distal end of the needle carrier 28 and matches in terms of shape and dimensions the third portion 63 and the beginning of the second portion 62 of the passage within the extension 60 of cylinder 1.

The passage zone of the extension 60 located on both sides of its constriction is filled with a body of an elastomer 66 sealing tightly the cylinder 1, while allowing the passage of the needle and the watertight closure of the passage 61, 62, 63 when the needle is retraced in the cylinder after use.

The proximal end of the needle carrier 28 has a conical form which expands towards the plunger 14 and its peripheral surface slides without clearance in this cylinder 1. This proximal end of the needle carrier 28 further comprises snap on means 67 cooperating with the snap on means 68 of the distal end of the plunger 14, to form a coupling which is irreversible once engaged.

The distal end of the plunger 14 slides without clearance in the cylinder 1 and comprises a front cavity 69 as well as a recess 70 opening sideways. The wall 71 separating the front cavity 69 from the recess 70 is provided with an opening 72.

In this embodiment of the syringe, the member with a lower resistance to compression when it is wet than when it is dry is formed by a cylinder or 73 having a central through hole 74.

This member 73 is fastened to the plunger by means of a stopper 75 comprising a head 76, the front part of which is truncated and a rod 77 extending through the element 73 and the wall 71 of the plunger 14. This rod 77 has a groove 78 which in the assembled position is situated in the recess 70 and receives a leaf spring 79 having a notch 80 allowing the passage of the rod 77 in its part with a diameter reduced by the groove 78. Thus, the member with a variable resistance 73 is maintained tightly in place by the pressure of the spring 79 between the head 76 of the stopper 75 and the wall 71 of the plunger 14.

Of course, the dimensions of these different elements are such that when the member with a variable resistance 73 is in its dry state and the needle carrier 28 enters in contact with the head 76 of the stopper 75 carried by the plunger 14 (see FIG. 22), it is possible to snap in place on the needle carrier 28 on the cylinder 1 by the coupling 64, 65, but the distance between the members of the snap on mechanism 67, 68 of the needle carrier 28 and of the plunger 14 is too large for the two to engage.

Figure 22:
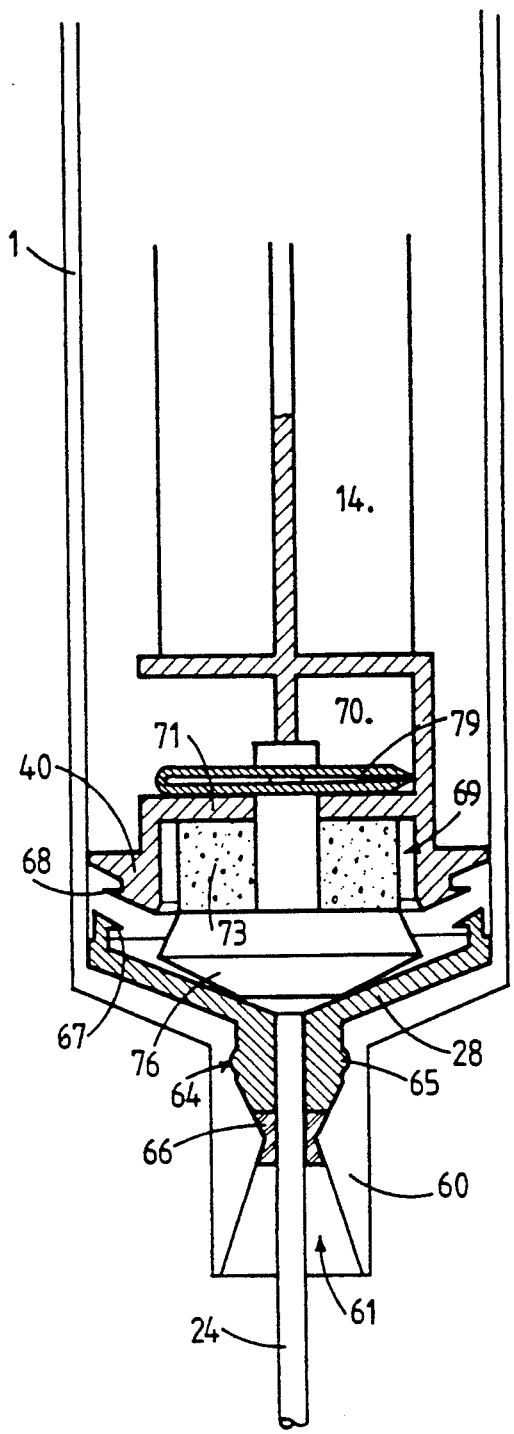
Figure 23:
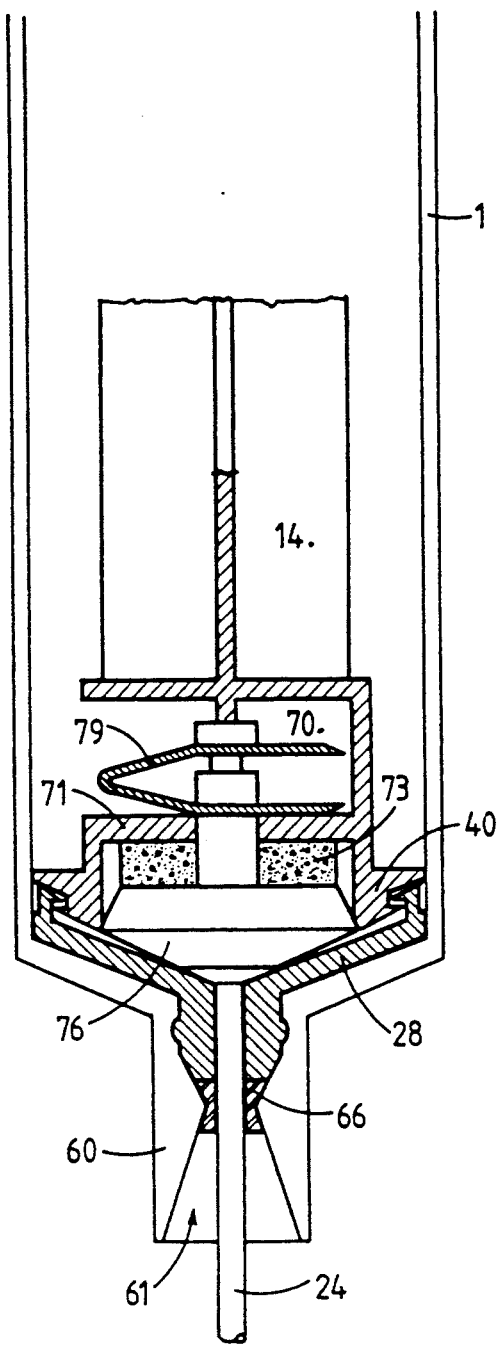
Figure 24:
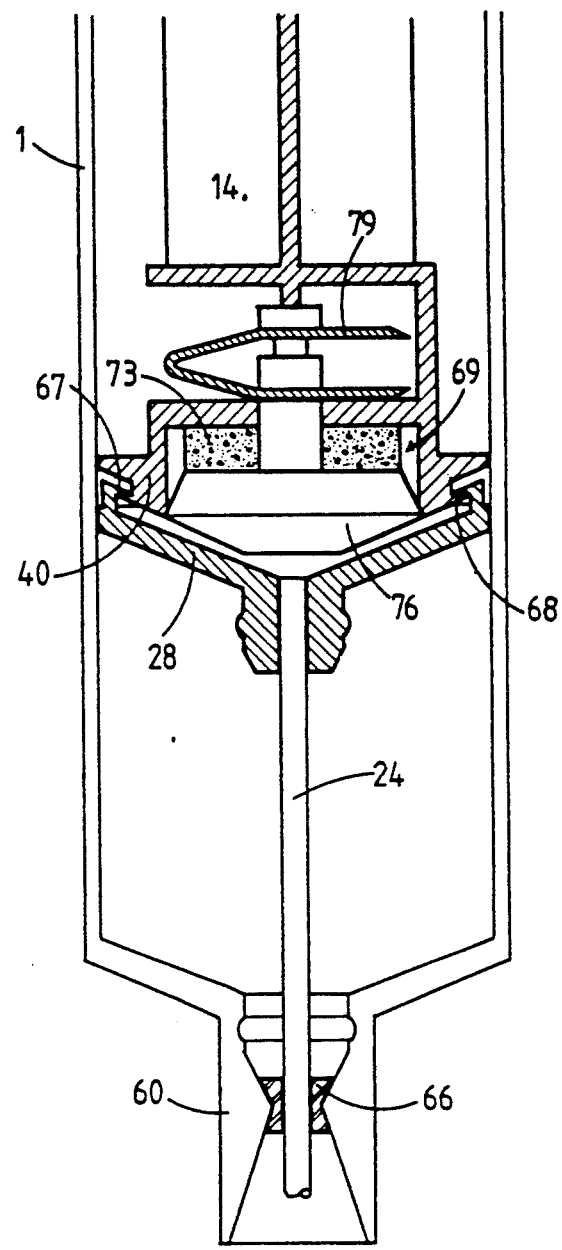

Thus, the needle carrier 28 can be pushed by the plunger 14 to make the needle protrude from the cylinder by piercing the elastomer and by coupling temporarily the needle carrier to the cylinder (FIG. 22).

When subsequently pulling the plunger 14 to draw the liquid into the cylinder, the member 73 softens upon contact with the liquid and is compressed by the action of the spring 79 and of the stopper 75, thus reducing the distance between the front part of the head 75 and the snap on means 68 of the plunger 14.

In this manner, at the end of the injection of the solution to a patient (FIG. 23), the plunger 14 is coupled permanently to the needle carrier 22 by the means 67, 88 and when the plunger 14 is pulled out, it pulls the needle carrier in such a manner as to retract, as was described previously, the needle 24 inside the cylinder 1 (FIG. 24).

In this embodiment also, means are provided so that at full retraction of the plunger, the needle carrier be pushed sideways by a spring, for example so that the needle 24 be oriented at an angle with respect to the axis of the cylinder and thus to prevent that the needle may be made to protrude again therefrom.

Apart from the question of the construction and of the shapes of the parts which are particularly well suited for a mass production, this embodiment offers the advantage that the compressible element 73 is, when wetted by the liquid entering the cylinder, compressed by the spring 79. This makes it possible to decrease the force necessary when the needle is pushed into its most forward position to engage permanently the plunger and the needle carrier.

Figure 27:
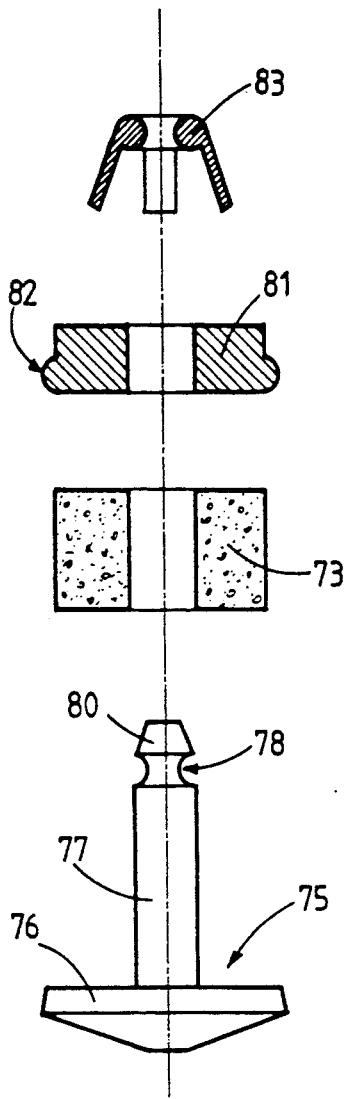
FIGS. 27 and 28 show another version of this fourth embodiment of the syringe.
Figure 28:
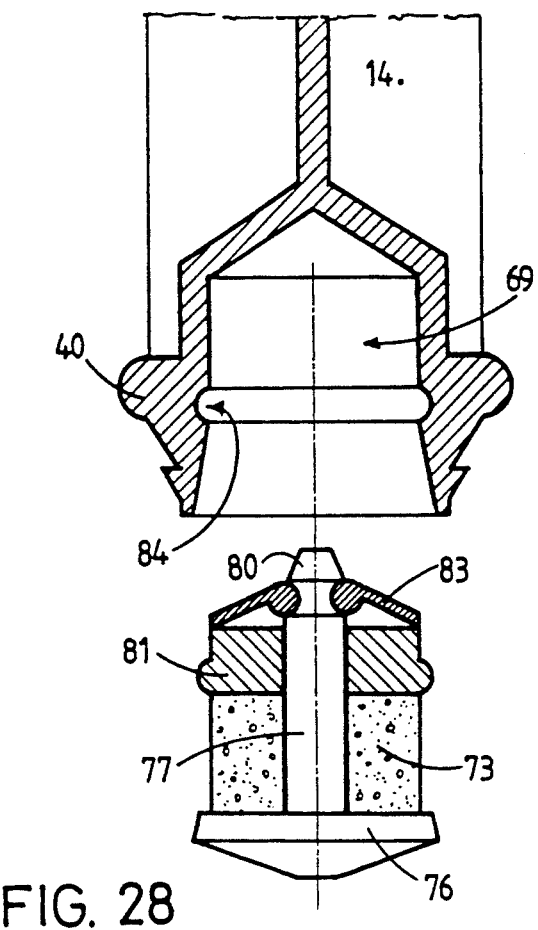

FIGS. 27 and 28 illustrate another version of this fourth embodiment of the invention, which concerns the fixation of the member 73 with a variable resistance when dry and when wet, on the plunger.

Here, this member 73 is slipped on the rod 77 of the stopper 75 and the proximal end of this rod comprises a groove 78 and a truncated end 80. A disk 81 is slipped on this rod 77 on top of the member 73 and a leaf spring 83 compresses the assembly and is snapped in the groove 78 of the rod 77 by its central opening.

This disk 81 carries a circular bead 82 which makes it possible to couple together the stopper assembly 75, the deformable member 73, the disk 81 and the spring 83 in the front recess 69 of the plunger 14 which comprises a circular groove 84 for receiving the bead of the disk 81.

The advantage of this version is that the assembly formed by the stopper 75, the member 73, the disk 81 and the spring 83 can be stored assembled. The assembling of the syringe is then all the simpler.

Figure 29:
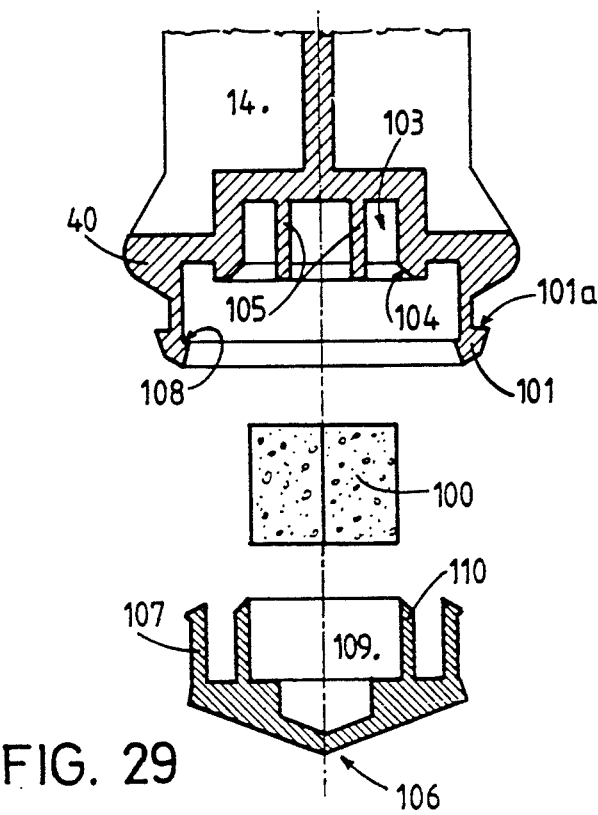
FIG. 29 shows another version of the fixation of the deformable member on the plunger.

FIG. 29 illustrates another version of the fixation of the compressible member 100, here of a cubic shape, the resistance of which to compression is greater when dry than when wet.

In this version, the distal end of the plunger 14 carries a cylindrical wall 101 with an outer flange 101a providing the non-disengageable part of the coupling with the needle carrier 28 (not illustrated) having mating coupling members. The front face of the plunger comprises a housing 103, the edges of which are chamfered at 104, the housing divided by the walls 105 acting as a stop for the compressible member 100.

A cap 106 the distal end of which has the same shape as that of the stopper 75 in the previous embodiment, but which is provided with a housing 109 for receiving the deformable member 100 and hooks 107 enabling the fixation of this cap to a retaining shoulder 108 carried by the cylindrical wall 101 of the plunger 14.

Thus, the member 100 can be fastened in its non-compressed dry state at the end of the plunger 14.

The housing 109 of the stopper 106 is defined by a wall 110 the end of which is chamfered and placed in such a manner as to come in contact with the chamfered edges 104 of the housing 103 of the plunger when the deformable member 100 is compressed.

Thus, in the wet and compressed state, member 100 is entirely trapped between the plunger head and the cap, for example in a watertight manner.

In this version, another part is omitted and the assemblage of the member 100 on the plunger is simplified accordingly.

In this version, one can also achieve an automatic compression of the compressible member 100 by providing a spring made of stainless steel which tends to pull together the cap 106 of the plunger head 14. Such a spring can be provided as a cylindrical ring, the outer wall of which is in contact with the internal surface of the cylindrical wall 101 of the plunger head. This ring is maintained in this position by the retaining shoulder. This ring comprises several tabs extending towards the center of the ring, which tabs take their bearing on the truncated front face of the cap 106. This front face can comprise recesses for this purpose.

Thus, owing to their inherent resiliency, the tabs tend to bring together the cap 106 and the front end of the plunger 14 and hence to compress the member with a variable resistance 100.

We claim:

1. A syringe for medical use comprising a watertight cylindrical body, a plunger movable linearly inside the body, a needle also movable linearly inside the body and relatively to the plunger, wherein before the syringe is used, the needle is located for protection inside the watertight cylindrical body; an elastomeric plug which can be perforated by the needle and that closes a distal end of the syringe; the plunger being movable to a first position in which the plunger has advanced the needle to a position in which the needle has penetrated said plug and is extended to a position of use, snap on coupling means non-releasably engageable between the plunger and the needle upon movement of the plunger to a second position beyond said first position in the direction of said advance of the needle, and a member within the syringe which has lesser resistance to compression when wet than when dry and which when dry limits movement of the plunger to said first position and which when wet permits movement of the plunger to said second position.

2. A syringe according to claim 1, wherein said snap on means when engaged retracts the needle upon retraction of the plunger to a position within the syringe out of contact with said plug and in which said snap on coupling means laterally deflects a distal end of the needle to a position in which the needle cannot again be pushed through the plug.

3. A syringe according to claim 1, wherein the needle is fastened fixedly to a needle carrier that is in slidable contact with the cylindrical body.

4. A syringe according to claim 1, wherein said member is a ring carried by the needle carrier.

5. A syringe according to claim 1, wherein said member is carried by a distal face of the plunger.

6. A syringe according to claim 1, wherein said member is carried by a proximal face of the needle carrier.

7. A syringe for medical use comprising a watertight cylindrical body, a plunger movable linearly inside the body, a needle carrier also movable linearly inside the body and relatively to the plunger, a needle carried by the needle carrier, wherein before the syringe is used, the needle is located for protection inside the watertight cylindrical body; and elastomeric plug which can be perforated by the needle and that closes a distal end of the syringe; first snap on coupling means engageable between the needle carrier and the distal end of the syringe upon movement of the plunger to a first position in which the plunger has advanced the needle carrier and needle to a position in which the first snap on coupling means is engaged and the needle has penetrated said plug and is extended to a position of use, second snap on coupling means non-releasably engageable between the plunger and the needle upon movement of the plunger to a second position beyond said first position in the direction of said advance of the needle, and a member within the syringe which has lesser resistance to compression when wet than when dry and which when dry limits movement of the plunger to said first position and which when wet permits movement of the plunger to said second position.

8. A syringe according to claim 7, wherein said second snap on means when engaged retracts the needle upon retraction of the plunger to a position within the syringe out of contact with said plug and needle carrier and in which said second snap on coupling means laterally deflects a distal end of the needle to a position in which the needle cannot again be extended through the plug.

9. A syringe according to claim 7, wherein said member is a ring carried by the needle carrier.

10. A syringe according to claim 7, wherein said member is carried by a distal face of the plunger.

11. A syringe according to claim 7, wherein said member is carried by a proximal face of the needle carrier.

12. A syringe according to claim 7, wherein said first snap on coupling means non-releasably engage said needle carrier and the distal end of the syringe, and further comprising third snap on coupling means between the needle and the needle carrier, said third snap on coupling means having a resistance to uncoupling sufficient to advance the needle through the plug but insufficient to prevent retraction of the plunger from said second position and separation of the needle from the needle carrier.

* * * * *